United States Patent
Ouh et al.

(10) Patent No.: US 10,509,171 B2
(45) Date of Patent: Dec. 17, 2019

(54) OPTICAL TREATMENT OPTICAL FIBER PROBE AND MANUFACTURING METHOD THEREFOR

(71) Applicant: TAIHAN FIBEROPTICS CO., LTD., Ansan-si (KR)

(72) Inventors: Chi Hwan Ouh, Anyang-si (KR); Chang Hyun Jung, Gunpo-si (KR); Ga Ye Park, Ansan-si (KR); Hyung Su Cho, Seoul (KR); Dae Young Kim, Ansan-si (KR); Jae Wan Han, Incheon (KR)

(73) Assignee: TAIHAN FIBEROPTICS CO., LTD., Ansan-si (KR)

( * ) Notice: Subject to any disclaimer, the term of this patent is extended or adjusted under 35 U.S.C. 154(b) by 0 days.

(21) Appl. No.: 16/341,053

(22) PCT Filed: Dec. 7, 2016

(86) PCT No.: PCT/KR2016/014283
§ 371 (c)(1),
(2) Date: Apr. 10, 2019

(87) PCT Pub. No.: WO2018/070607
PCT Pub. Date: Apr. 19, 2018

(65) Prior Publication Data
US 2019/0235161 A1    Aug. 1, 2019

(30) Foreign Application Priority Data

Oct. 10, 2016 (KR) .......................... 10-2016-0130806

(51) Int. Cl.
*G02B 6/26* (2006.01)
*G02B 6/02* (2006.01)
(Continued)

(52) U.S. Cl.
CPC .............. *G02B 6/262* (2013.01); *A61B 18/22* (2013.01); *A61N 5/062* (2013.01); *G02B 6/02052* (2013.01); *G02B 6/02309* (2013.01)

(58) Field of Classification Search
CPC .............. G02B 6/0008; G02B 6/02052; G02B 6/02309; G02B 6/02333; G02B 6/02395;
(Continued)

(56) References Cited

U.S. PATENT DOCUMENTS 5,976,175 A * 11/1999 Hirano ................... A61N 5/062
606/15
8,139,911 B2 * 3/2012 Konishi ............. A61B 1/00096
385/123
(Continued)

*Primary Examiner* — Michael P Mooney
(74) *Attorney, Agent, or Firm* — Lex IP Meister, PLLC

(57) ABSTRACT

Disclosed is an optical fiber probe for an optical treatment including a core, to which incident light is guided, a cladding disposed to surround the core, a side surface divergence part connected to the core and configured to diverge the incident light guided to the core to a side surface of a cylindrical column, a diffusion layer disposed to surround the side surface divergence part, a distal end divergence part connected to the side surface divergence part, having a cylindrical shape, and configured to diverge the incident light guided to the side surface divergence part to the outside, and a coating layer disposed to surround the cladding and the diffusion layer and configured to seal the cladding and the diffusion layer, wherein the refractive index of the cladding is lower than the refractive index of the core, the refractive index of the diffusion layer is higher than the refractive index of the core, and the refractive index of the coating layer is higher than the refractive indices of the cladding and the diffusion layer.

5 Claims, 4 Drawing Sheets

(51) Int. Cl.
*A61B 18/22* (2006.01)
*A61N 5/06* (2006.01)

(58) Field of Classification Search
CPC .......... G02B 6/241; G02B 6/245; G02B 6/25;
G02B 6/262; A61B 18/00; A61B 18/18;
A61B 18/22; A61B 2018/00577; A61B
2018/00964; A61N 5/00; A61N 5/06;
A61N 5/0601; A61N 5/0613; A61N
5/062; A61N 2005/0612; A61N 2005/063;
A61N 2005/0643
USPC ............ 385/27, 28, 31, 35, 38, 39, 123–128
See application file for complete search history.

(56) References Cited

U.S. PATENT DOCUMENTS

| | | | |
|---|---|---|---|
| 2002/0138073 A1* | 9/2002 | Intintoli | A61B 18/22 606/15 |
| 2006/0018596 A1* | 1/2006 | Loebel | A61B 18/22 385/38 |

* cited by examiner

OPTICAL TREATMENT OPTICAL FIBER PROBE AND MANUFACTURING METHOD THEREFOR

TECHNICAL FIELD

The present invention relates to an optical fiber probe for an optical treatment and a method for manufacturing the same, and more particularly, to an an optical fiber probe for an optical treatment which has a side surface divergence part, which diverges incident light to a side surface of the optical fiber probe spaced apart from a distal end of the optical fiber probe by a specific length and a distal end divergence part having a spherical shape at a distal end of the optical fiber probe, and can effectively improve chemical-resistant and heat-resistant characteristics while restraining external foreign substances from intruding to the interior of the optical fiber probe, and a method for manufacturing the same.

BACKGROUND ART

In general, an optical treatment is performed by irradiating a light source, such as a light emitting diode (LED), a laser, or the like, to abnormal tissues (lesion tissues), and includes destruction of lesion tissues, (a surgery of) cutting lesion tissues, a hot heat treatment, a photo dynamic therapy (PDT), and the like. Among the optical treatment methods, a therapy of inserting an optical fiber probe or the like into the human body and irradiating light after the optical fiber probe approaches the corresponding portion in order to treat lesion tissues generated in the human body has been suggested, but a problem of generating a chemical reaction in the human body, causing a fire or oxidation, occurs.

Meanwhile, in order to solve the problems, a scheme of finishing an end of the optical fiber probe with cover glass or the like has been suggested. However, the solution can restrain the chemical reaction in the human body but it is difficult to apply the scheme to an optical fiber probe of unit of μm.

The prior technology of the present invention is disclosed in Korean Patent Application Publication No. 10-2015-0025543.

DETAILED DESCRIPTION OF THE INVENTION

Technical Problem

In order to solve the above-mentioned problems, the present invention provides an an optical fiber probe for an optical treatment which has a side surface divergence part, which diverges incident light to a side surface of the optical fiber probe spaced apart from a distal end of the optical fiber probe by a specific length and a distal end divergence part having a spherical shape at a distal end of the optical fiber probe, and can effectively improve chemical-resistant and heat-resistant characteristics while restraining external foreign substances from intruding to the interior of the optical fiber probe.

The present invention also provides a method for manufacturing an optical fiber probe for an optical treatment, by which the optical fiber probe for an optical treatment can be easily manufactured.

Technical Solution

In accordance with an aspect of the present invention, there is provided an optical fiber probe for an optical treatment including a core, to which incident light is guided, a cladding disposed to surround the core, a side surface divergence part connected to the core and configured to diverge the incident light guided to the core to a side surface of a cylindrical column, a diffusion layer disposed to surround the side surface divergence part, a distal end divergence part connected to the side surface divergence part, having a cylindrical shape, and configured to diverge the incident light guided to the side surface divergence part to the outside, and a coating layer disposed to surround the cladding and the diffusion layer and configured to seal the cladding and the diffusion layer, wherein the refractive index of the cladding is lower than the refractive index of the core, the refractive index of the diffusion layer is higher than the refractive index of the core, and the refractive index of the coating layer is higher than the refractive indices of the cladding and the diffusion layer.

It is preferable that the core, the side divergence part, and the distal end divergence part are integrally formed.

It is preferable that the side surface of the cylindrical column of the side surface divergence part has a concavely curved shape.

It is preferable that a circular section of the cylindrical column of the side surface divergence part has a concavely curved shape which is symmetrical.

In accordance with another aspect of the present invention, there is provided a method for manufacturing an optical fiber probe for an optical treatment, the method including removing a specific portion of a cladding disposed to surround the core, to which incident light is guided, processing a side surface divergence part having a concavely curved shape on a cylindrical side surface of the core, from which the specific portion of the cladding is removed, processing a distal end divergence part which is connected to the side surface divergence part and the distal end divergence part and has a spherical shape, processing a coating layer disposed to surround the cladding and the side surface divergence part, processing a diffusion layer by injecting a material, the refractive index of which is higher than the refractive index of the core such that the diffusion layer surrounds the side surface divergence part, and processing the coating layer such that the coating layer seals the cladding and the diffusion layer, wherein the refractive index of the cladding is lower than the refractive index of the core and the refractive index of the coating layer is higher than the refractive indices of the cladding and the diffusion layer.

Advantageous Effects of the Invention

The optical fiber probe for an optical treatment according to the embodiments of the present invention has a side surface divergence part, which diverges incident light to a side surface of the optical fiber probe spaced apart from a distal end of the optical fiber probe by a specific length and a distal end divergence part having a spherical shape at a distal end of the optical fiber probe, and thus can effectively improve chemical-resistant and heat-resistant characteristics while restraining external foreign substances from intruding to the interior of the optical fiber probe.

Further, the optical fiber probe for an optical treatment according to the embodiments of the present invention includes the side surface divergence part having a concavely curved shape on the side surface of the cylindrical column, and thus can effectively improve the uniformity of light emission.

BEST MODE

Figure 1:
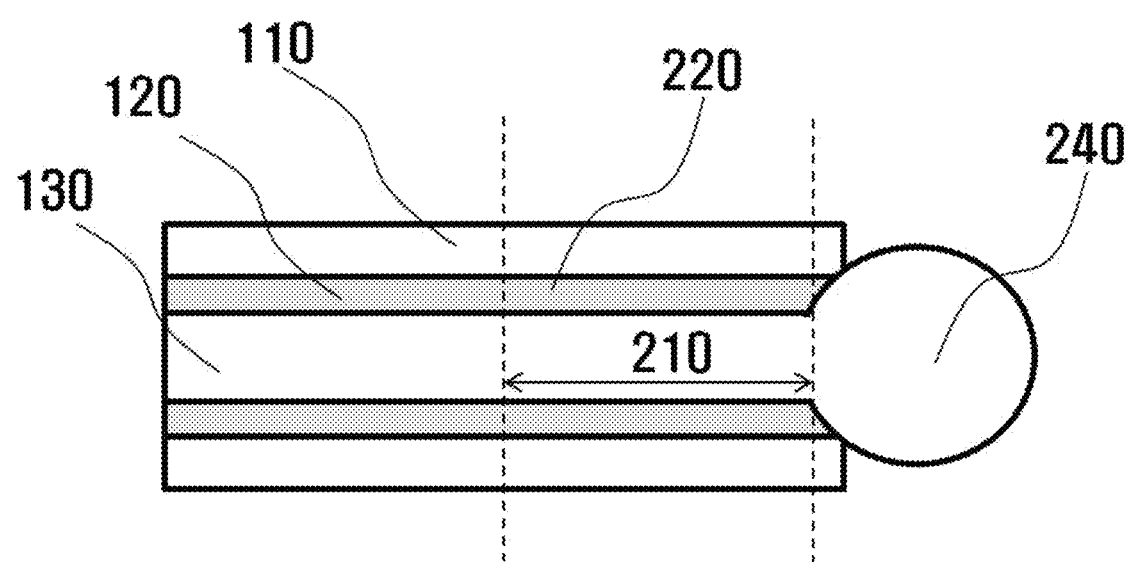
FIG. 1 is a transverse sectional view of an optical fiber probe for an optical treatment according to an embodiment of the present invention.

Details of the other embodiments are included in the detailed description and the accompanying drawings.

The above and other aspects, features and advantages of the invention will become apparent from the following description of the following embodiments given in conjunction with the accompanying drawings. However, the present invention is not limited to the embodiments disclosed below, but may be implemented in various forms. The embodiments of the present invention is provided to make the disclosure of the present invention complete and fully inform those skilled in the art to which the present invention pertains of the scope of the present invention. The same reference numerals denote the same elements throughout the specification.

As illustrated in FIG. 1, an optical fiber probe for an optical treatment according to an embodiment of the present invention may include a core 130 to which incident light is guided, a cladding 120 disposed to surround the core 130, a side surface divergence part 210 which is connected to the core 130 and diverges the incident light guided to the core 130 to a side surface of a cylindrical column, a diffusion layer 220 disposed to surround the side surface divergence part 210, a distal end divergence part 240 which is connected to the side surface divergence part 210, has a spherical shape, diverges the incident light guided to the side surface divergence part 210 to the outside, and a coating layer 110 which is disposed to surround the cladding 120 and the diffusion layer 220 and seals the cladding 120 and the diffusion layer 220.

Here, the refractive index of the cladding 120 is lower than the refractive index of the core 130, the refractive index of the diffusion layer 220 is higher than the refractive index of the core 130, and the refractive index of the coating layer 110 is higher than the refractive indices of the cladding 120 and the diffusion layer 220.

In detail, the core 130 and the cladding 120 may be manufactured of silica, an organic material, and the like, and the core 130, the side surface divergence part 210, and the distal end divergence part 240 may be integrally formed of the same material.

Further, the diffusion layer 220 may be manufactured of UV curing epoxy, thermosetting epoxy, 2-liquid type epoxy, and the like, and because the coating layer 110 is manufactured of a material having heat-resistant and chemical-resistant characteristics to pass a biological safety inspection when it is inserted into a human body, it may be manufactured of poly ether ether ketone (PEEK), ethylene tetra fluoro ethylene (ETFE), per fluoro alkoxy (PFA), poly tetra fluoro ethylene (PTFE), and the like.

Figure 2:
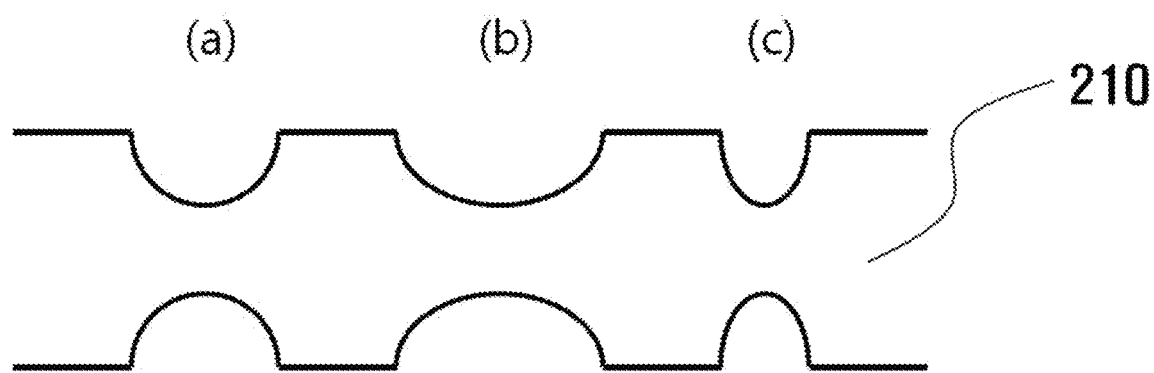
FIG. 2 is a transverse sectional view of a side surface divergence part of the optical fiber probe for an optical treatment according to the embodiment of the present invention.
Figure 3:
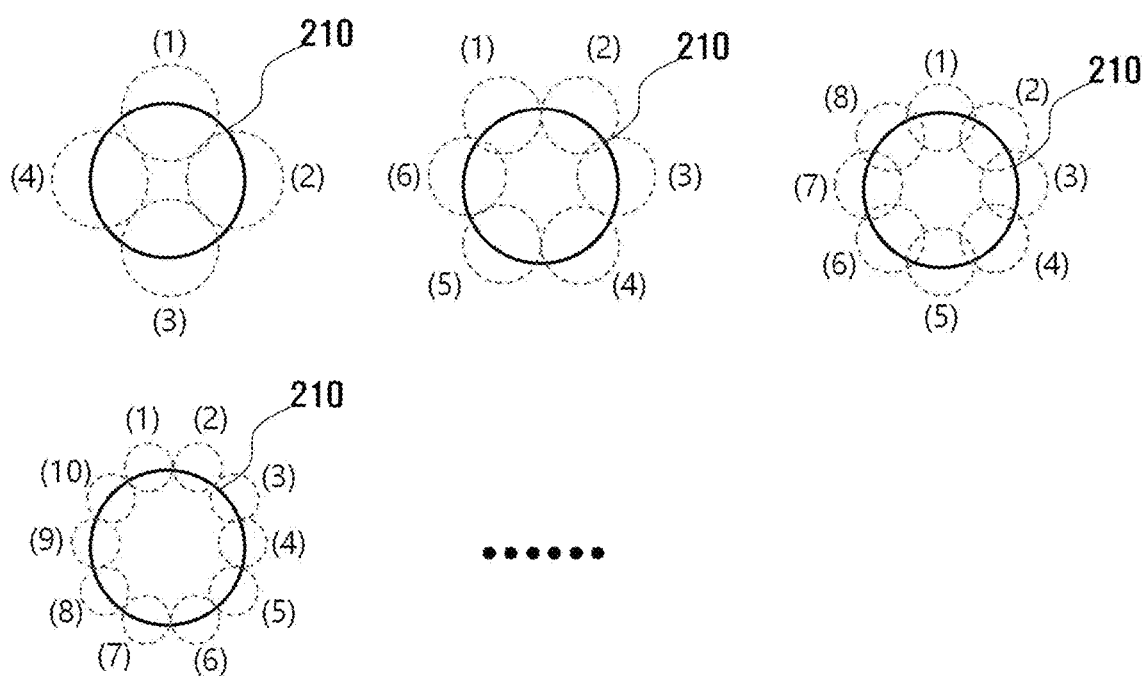
FIG. 3 is a longitudinal sectional view of the side surface divergence part of the optical fiber probe for an optical treatment according to the embodiment of the present invention.

Meanwhile, as illustrated in FIG. 2, a cylindrical side surface of the side surface divergence part 210 has a concavely curved surface, and as illustrated in FIG. 3, a circular section of the cylindrical column of the side divergence part 210 has a concavely curved shape, which is symmetrical.

According to a method for manufacturing an optical fiber probe for an optical treatment according to an embodiment of the present invention, first, a specific portion of the cladding 120 disposed to surround the core 130 is removed.

Next, the side surface divergence part 210, which has a concavely curved shape on the side surface of the cylindrical column of the core 130, from which the specific portion of the cladding 120 is removed, is processed and the distal end divergence part 240 which is connected to the side surface divergence part 210 and has a cylindrical shape is processed.

Figure 4:
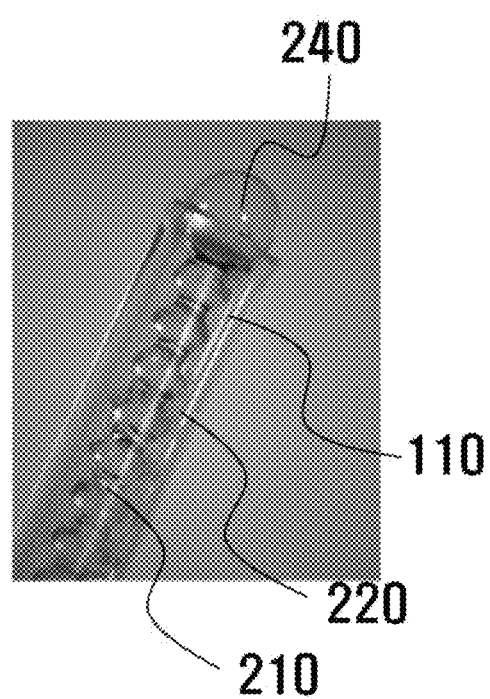
FIG. 4 is a perspective view of the optical fiber probe for an optical treatment according to an embodiment of the present invention.

Next, the coating layer 110 disposed to surround the cladding 120 and the side surface divergence part 210 is processed, the diffusion layer 220 is processed by injecting a material, the refractive index of which is higher than the refractive index of the core 130 such that the diffusion layer 220 surrounds the side surface diffusion part 210, and as illustrated in FIG. 4, the coating layer 110 is processed to seal the cladding 120 and the diffusion layer 220.

It will be understood by an ordinary person skilled in the art to which the present invention pertains that the present invention may be carried out in other detailed forms than the disclosed embodiments without changing the technical spirit or the essential features.

Therefore, the above-described embodiments are exemplary in all aspects, and should be construed not to be restrictive.

The scope of the present invention is determined by the claims rather than the description of the invention, and all changes or modifications derived from the meanings and scopes of the claims and the equivalents thereof are construed to be included in the scope of the present invention.

The invention claimed is:

1. An optical fiber probe for an optical treatment comprising:
    a core, to which incident light is guided;
    a cladding disposed to surround the core;
    a side surface divergence part connected to the core and configured to diverge the incident light guided to the core to a side surface of a cylindrical column;
    a diffusion layer disposed to surround the side surface divergence part;
    a distal end divergence part connected to the side surface divergence part, having a cylindrical shape, and configured to diverge the incident light guided to the side surface divergence part to the outside; and
    a coating layer disposed to surround the cladding and the diffusion layer and configured to seal the cladding and the diffusion layer,
    wherein the refractive index of the cladding is lower than the refractive index of the core, the refractive index of the diffusion layer is higher than the refractive index of the core, and the refractive index of the coating layer is higher than the refractive indices of the cladding and the diffusion layer.

2. The optical fiber probe for an optical treatment of claim 1, wherein the core, the side divergence part, and the distal end divergence part are integrally formed.

3. The optical fiber probe for an optical treatment of claim 1, wherein the side surface of the cylindrical column of the side surface divergence part has a concavely curved shape.

4. The optical fiber probe for an optical treatment of claim 3, wherein a circular section of the cylindrical column of the side surface divergence part has a concavely curved shape which is symmetrical.

5. A method for manufacturing an optical fiber probe for an optical treatment, the method comprising:
- removing a specific portion of a cladding disposed to surround the core, to which incident light is guided;
- processing a side surface divergence part having a concavely curved shape on a cylindrical side surface of the core, from which the specific portion of the cladding is removed;
- processing a distal end divergence part which is connected to the side surface divergence part and the distal end divergence part and has a spherical shape;
- processing a coating layer disposed to surround the cladding and the side surface divergence part;
- processing a diffusion layer by injecting a material, the refractive index of which is higher than the refractive index of the core such that the diffusion layer surrounds the side surface divergence part; and
- processing the coating layer such that the coating layer seals the cladding and the diffusion layer, wherein the refractive index of the cladding is lower than the refractive index of the core and the refractive index of the coating layer is higher than the refractive indices of the cladding and the diffusion layer.

\* \* \* \* \*